United States Patent
Jacobsen et al.

(10) Patent No.: US 10,321,804 B2
(45) Date of Patent: Jun. 18, 2019

(54) ARTICULATED TIP PART FOR AN ENDOSCOPE

(71) Applicant: Ambu A/S, Ballerup (DK)

(72) Inventors: Morten Jacobsen, Hørsholm (DK); Troels Nicolaj Qvist, Roskilde (DK)

(73) Assignee: AMBU A/S, Ballerup (DK)

( * ) Notice: Subject to any disclaimer, the term of this patent is extended or adjusted under 35 U.S.C. 154(b) by 96 days.

(21) Appl. No.: 14/759,044

(22) PCT Filed: Jan. 7, 2013

(86) PCT No.: PCT/DK2013/050002
§ 371 (c)(1),
(2) Date: Jul. 2, 2015

(87) PCT Pub. No.: WO2014/106511
PCT Pub. Date: Jul. 10, 2014

(65) Prior Publication Data
US 2015/0335227 A1 Nov. 26, 2015

(51) Int. Cl.
*A61B 1/00* (2006.01)
*A61B 1/005* (2006.01)
*A61B 1/018* (2006.01)
*A61B 1/05* (2006.01)

(52) U.S. Cl.
CPC .......... *A61B 1/0008* (2013.01); *A61B 1/0055* (2013.01); *A61B 1/00114* (2013.01); *A61B 1/018* (2013.01); *A61B 1/05* (2013.01)

(58) Field of Classification Search
CPC .......... A61M 25/0054; A61M 25/0013; A61M 25/0138; A61B 1/0055; A61B 2017/00309
USPC .................................................. 600/141, 142
See application file for complete search history.

(56) References Cited

U.S. PATENT DOCUMENTS

| 4,580,551 A * | 4/1986 | Siegmund ............ A61B 1/0055 600/139 |
| 4,651,718 A * | 3/1987 | Collins ................ A61B 1/0055 138/120 |
| 4,706,653 A | 11/1987 | Yamamoto |
| 4,745,470 A | 5/1988 | Yabe et al. |
| 4,778,247 A | 10/1988 | Carpenter |

(Continued)

FOREIGN PATENT DOCUMENTS

| CN | 103228199 | 7/2013 |
| JP | 2005152043 | 6/2005 |

(Continued)

OTHER PUBLICATIONS

In corresponding International Application No. PCT/DK2013/050002, International Search Report, dated Sep. 12, 2013; 2 pages and International Preliminary Report on Patentability; dated Jul. 7, 2015; 7 pages.

*Primary Examiner* — Alexandra L Newton
*Assistant Examiner* — Rynae Boler
(74) *Attorney, Agent, or Firm* — Faegre Baker Daniels LLP

(57) ABSTRACT

An articulated tip part (3) for an endoscope (1). The articulated tip part (3) comprises a distal end segment (4), a proximal end segment (6) and a number of intermediate segments (5) arranged between the distal end segment (4) and the proximal end segment (6). Each intermediate segment (5) comprises a first passage (8) adapted to accommodate and support an outer wall (11) of a tube (9) providing a working channel of the endoscope (1).

19 Claims, 3 Drawing Sheets

(56) References Cited

U.S. PATENT DOCUMENTS

| | | | |
|---|---|---|---|
| 4,832,003 A | 5/1989 | Yabe | |
| 4,856,495 A | 8/1989 | Tohjoh et al. | |
| 4,860,732 A | 8/1989 | Hasegawa et al. | |
| 4,911,148 A | 3/1990 | Sosnowski et al. | |
| 4,918,521 A | 4/1990 | Yabe et al. | |
| 5,089,895 A | 2/1992 | Fraker et al. | |
| 5,376,960 A | 12/1994 | Wurster | |
| 5,379,756 A | 1/1995 | Pileski et al. | |
| 5,418,566 A | 5/1995 | Kameishi | |
| 5,438,975 A | 8/1995 | Miyagi et al. | |
| 5,547,457 A | 8/1996 | Tsuyuki et al. | |
| 5,830,401 A | 11/1998 | Prichard et al. | |
| 5,966,168 A | 10/1999 | Miyazaki | |
| 6,004,263 A | 12/1999 | Nakaichi | |
| 6,110,104 A | 8/2000 | Suzuki et al. | |
| 6,302,616 B1* | 10/2001 | Takahashi | B23K 26/244 |
| | | | 219/121.64 |
| 6,456,863 B1 | 9/2002 | Levin et al. | |
| 7,455,806 B2 | 11/2008 | Junger et al. | |
| 7,758,495 B2 | 7/2010 | Pease et al. | |
| 8,182,422 B2 | 5/2012 | Bayer et al. | |
| 8,547,424 B2 | 10/2013 | Ishii et al. | |
| 8,790,250 B2 | 7/2014 | Petersen et al. | |
| 9,125,582 B2 | 9/2015 | Petersen | |
| 9,220,400 B2 | 12/2015 | Petersen | |
| 9,486,595 B2 | 11/2016 | Borrye et al. | |
| 9,572,482 B2 | 2/2017 | Lin | |
| 9,622,649 B2 | 4/2017 | Lin | |
| 2002/0022765 A1 | 2/2002 | Belson | |
| 2003/0056540 A1 | 3/2003 | Mukasa et al. | |
| 2004/0199052 A1* | 10/2004 | Banik | A61B 1/00071 |
| | | | 600/142 |
| 2004/0242963 A1* | 12/2004 | Matsumoto | A61B 1/00096 |
| | | | 600/127 |
| 2005/0070759 A1* | 3/2005 | Armstrong | A61B 1/0051 |
| | | | 600/105 |
| 2005/0075538 A1 | 4/2005 | Banik et al. | |
| 2005/0131279 A1* | 6/2005 | Boulais | A61B 1/00059 |
| | | | 600/141 |
| 2005/0140068 A1 | 6/2005 | Junger et al. | |
| 2005/0154262 A1 | 7/2005 | Banik et al. | |
| 2005/0119527 A1 | 9/2005 | Ellis et al. | |
| 2005/0203341 A1 | 9/2005 | Welker et al. | |
| 2005/0234499 A1 | 10/2005 | Olson et al. | |
| 2006/0178556 A1 | 8/2006 | Hasser et al. | |
| 2007/0129466 A1 | 6/2007 | Kagawa et al. | |
| 2007/0249896 A1 | 10/2007 | Goldfarb et al. | |
| 2007/0249907 A1 | 10/2007 | Boulais | |
| 2008/0221393 A1* | 9/2008 | Padget | A61B 17/29 |
| | | | 600/142 |
| 2008/0249483 A1* | 10/2008 | Slenker | A61B 1/0055 |
| | | | 604/275 |
| 2008/0268559 A1 | 10/2008 | Jung | |
| 2008/0287741 A1* | 11/2008 | Ostrovsky | A61B 1/00071 |
| | | | 600/141 |
| 2009/0054728 A1* | 2/2009 | Trusty | A61B 1/00135 |
| | | | 600/114 |
| 2009/0177040 A1* | 7/2009 | Lyons | A61B 1/0055 |
| | | | 600/141 |
| 2009/0209819 A1 | 8/2009 | Kitagawa et al. | |
| 2010/0210905 A1 | 8/2010 | Takeuchi et al. | |
| 2010/0217082 A1 | 8/2010 | Ito et al. | |
| 2010/0280316 A1 | 11/2010 | Dietz et al. | |
| 2010/0324367 A1 | 12/2010 | Matsumoto et al. | |
| 2011/0251519 A1* | 10/2011 | Romoscanu | A61M 25/0013 |
| | | | 600/585 |
| 2012/0029281 A1 | 2/2012 | Frassica et al. | |
| 2012/0165608 A1 | 6/2012 | Banik et al. | |
| 2014/0114129 A1* | 4/2014 | Peh | A61B 1/00082 |
| | | | 600/141 |
| 2015/0366436 A1 | 12/2015 | Iuel | |
| 2016/0101254 A1 | 4/2016 | Hansen | |

FOREIGN PATENT DOCUMENTS

| | | |
|---|---|---|
| KR | 20120056363 | 6/2012 |
| WO | WO 2007/124211 | 11/2007 |
| WO | 2010066787 | 6/2010 |
| WO | 2010066788 | 6/2010 |
| WO | 2010066789 | 6/2010 |
| WO | 2010066790 | 6/2010 |
| WO | WO 2010/067765 | 6/2010 |
| WO | 2014106510 | 7/2014 |
| WO | 2016188537 | 12/2016 |
| WO | 2016188538 | 12/2016 |
| WO | 2016188539 | 12/2016 |
| WO | 2016188540 | 12/2016 |
| WO | 2016188541 | 12/2016 |
| WO | 2016188542 | 12/2016 |
| WO | 2016188543 | 12/2016 |

* cited by examiner

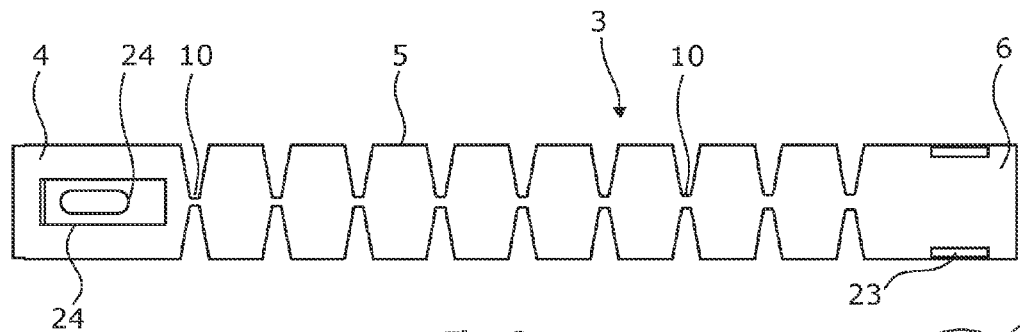
Fig. 8
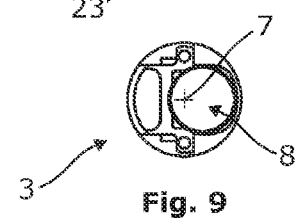
Fig. 9
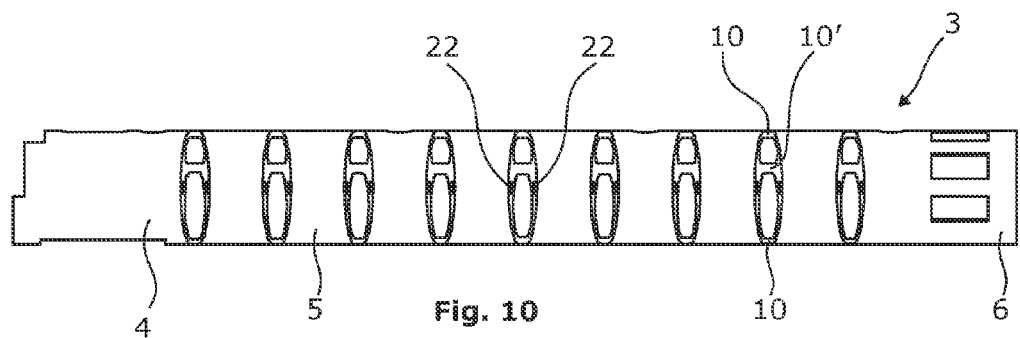
Fig. 10
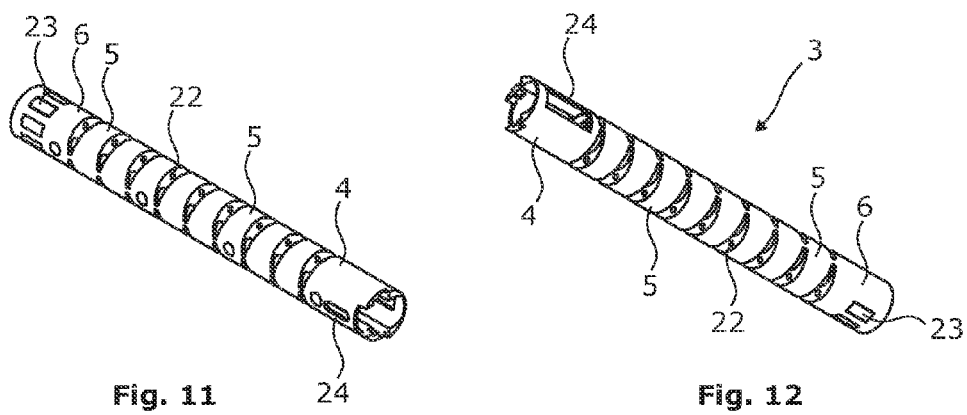
Fig. 11
Fig. 12

ARTICULATED TIP PART FOR AN ENDOSCOPE

CROSS REFERENCE TO RELATED APPLICATION

This is a § 371 application of International Application No. PCT/DK2013/050002, entitled "An Articulated Tip Part For An Endoscope," filed on Jan. 7, 2013, the full disclosure of which is expressly incorporated herein by reference in its entirety.

TECHNICAL FIELD

The present invention relates to endoscopes, and more specifically to an articulated tip part for an endoscope.

BACKGROUND OF THE DISCLOSURE

Endoscopes are well known devices for visually inspecting inaccessible places such as human body cavities. Typically, the endoscope comprises an elongated insertion tube with a handle at the proximal end as seen from the operator and visual inspections means, such as a built in camera, at the distal end of the elongated insertion tube. Electrical wiring for the camera and other electronics such as LED lighting run along the inside of the elongated insertion tube from the handle to the tip at the distal end. Instead of using cameras, endoscopes may also be fibre-optic, in which case the optical fibres run along inside of the elongated insertion tube.

In order to be able to manoeuvre the endoscope inside the body cavity, the distal end of the endoscope may comprise a section with increased flexibility, e.g. an articulated tip part allowing the operator to bend this section. Typically this is done by tensioning or slacking pull wires also running along the inside of the elongated insertion tube from the articulated tip part to a control mechanism of the handle. Furthermore, a working channel may run along the inside of the insertion tube from the handle to the tip, e.g. allowing liquid to be removed from the body cavity or allowing the insertion of surgical instruments or the like into the body cavity.

U.S. Pat. No. 4,911,148 discloses a fibre-optic endoscope with an articulated tip part. The articulated tip part is an integrally moulded member with cut-out progressively increasing in size towards the distal end. The cut-outs are provided in one side only, thus only allowing the bending of the articulated tip in one direction. The articulated tip comprises a central working channel. The pull wire and the fibre-optic cables are located in lumens arranged in the wall part of the articulated tip part.

US-A-2004/0199052 discloses a camera endoscope with an articulated tip part. The articulated tip comprises a central lumen. Though not clearly described, a working channel appears to be arranged in this central lumen. All cables except the pull wires are also arranged in this central lumen. The pull wires are located in lumens arranged in the wall part of the articulated tip part.

U.S. Pat. No. 4,580,551 discloses an articulated tip part for a fibre-optic endoscope. The cross-section of the articulated tip part comprises several lumens. In one of the lumens a tube for air or water is provided. This tube is comparatively narrow and will not be able to serve as a working channel as such.

SUMMARY OF DISCLOSED EMBODIMENTS

Based on the above prior at it is an object of the present invention to provide an improved articulated tip part for an endoscope.

According to a first aspect of the invention this object is achieved by an articulated tip part for an endoscope where the articulated tip part comprises a distal end segment, a proximal end segment and a number of intermediate segments arranged between the distal end segment and the proximal end segment, each intermediate segment comprising a passage, characterized in that the passage is adapted to accommodate and support an outer wall of a tube providing a working channel of the endoscope.

Adapting the passage to accommodate and support the outer wall of the tube providing the working channel allows the use of a large diameter tube with a relatively thin wall because the support provided by the passage through the individual segments makes the tube less prone to kinking when bending and/or collapsing when vacuum suction is applied. Having a large diameter tube with a relatively thin wall, in turn, provides for a large working channel, through which tools may be inserted and/or fluids withdrawn.

According to a preferred embodiment of the invention, the intermediate segments have a generally circular cross-section with a centre and the passage is off-set with respect to said centre. This allows the diameter of the working channel to be further increased. Preferably, the diameter is so large that centre of the generally circular cross-section of the segments lies within the passage.

According to a further preferred embodiment of the invention, each of said intermediate segments comprises a further passage adapted for accommodating electrical wires. Thus the working channel is separated from the electrical wires.

According to another preferred embodiment of the invention, adjacent intermediate segments are connected via flexible hinge members arranged in a plane corresponding to the first diameters of the cross-sections said two adjacent segments. This allows the location of the passage for the working channel and the further passages in the bending plane, thus providing maximum radius of the curvature of the working channel when bending, thus further reducing the risk kinking of collapsing of the tube.

According to another preferred embodiment of the invention, at least some of the flexible hinge members are adapted to engage and support the outer wall of the tube providing said working channel of the endoscope. Having the hinge members engage the outer wall of the tube further supports the tube. The tube thus becomes even less prone to kinking and/or collapsing.

According to yet a further preferred embodiment of the invention, the individual thickness of the flexible members decreases from one to the next in the direction from the proximal end segment to the distal end segment. Thus, the bending ability increases towards the distal end, which, in turn, increases manoeuvrability.

According to another preferred embodiment of the invention, pull wire passages are arranged symmetrically opposite each other on a second diameter orthogonal to and on either side of the first diameter in each of said intermediate segments. This allows the pull wire passages to be located where the wall thickness of the segment is the largest, thus giving good support against the forces occurring when the pull wires are tensioned.

According to yet another preferred embodiment of the invention, the distal end segment, the proximal end segment and said number of intermediate segments is provided as a one-piece integrally moulded part. This facilitates manufacturing in a cost-efficient manner.

According to another preferred embodiment of the present invention, the surface of at least some of the segments comprises recesses or cut outs. This ensures good connections between the articulated tip part and other parts of the endoscope, such as the plastic material moulded around the camera and electronics, adhesion to the outer sheath of the elongated insertion tube and the like.

According to a second aspect of the invention an endoscope comprising an articulated tip part as described above is provided.

According to a preferred embodiment of the second aspect of the invention, the tube providing the working channel comprises a first section and a second section along the length thereof, wherein the second section has a higher degree of flexibility than the first section. This provides the working channel with a high degree of flexibility where it needs to bend in tight curves, but is supported by the segments of articulated tip part according to the first aspect of the invention.

BRIEF DESCRIPTION OF THE DRAWINGS

The present invention will now be described in greater detail based on non-limiting exemplary embodiments, and with reference to the drawings on which:

FIGS. 8 to 12 show various views of a second embodiment of the articulated tip part according to the invention.

DETAILED DESCRIPTION

Figures 1, 2:
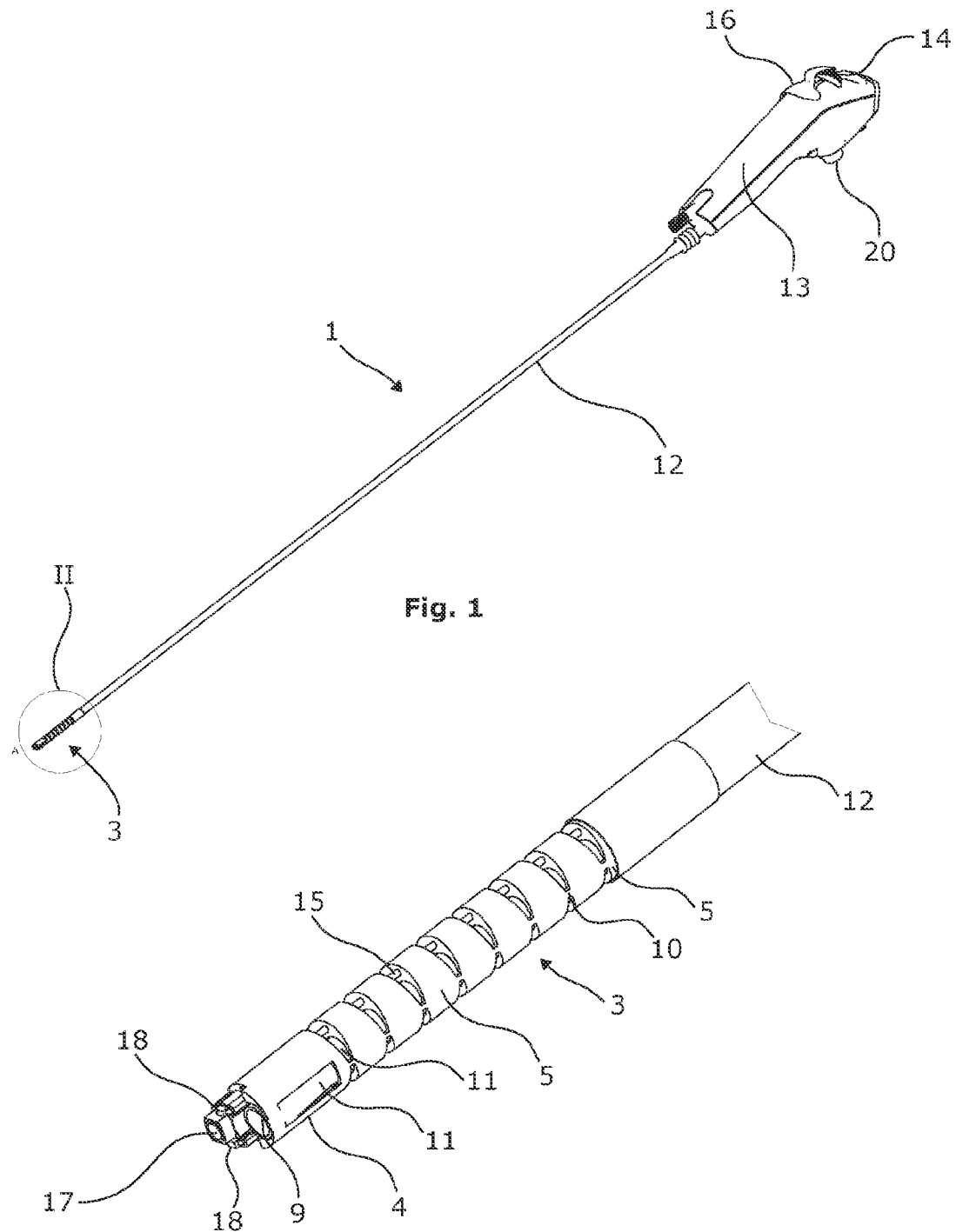
FIG. 1 shows an endoscope with an articulated tip part according to the invention at the distal end of the insertion tube.
FIG. 2 shows details of the articulated tip part at the distal end of the insertion tube.
Figure 3:
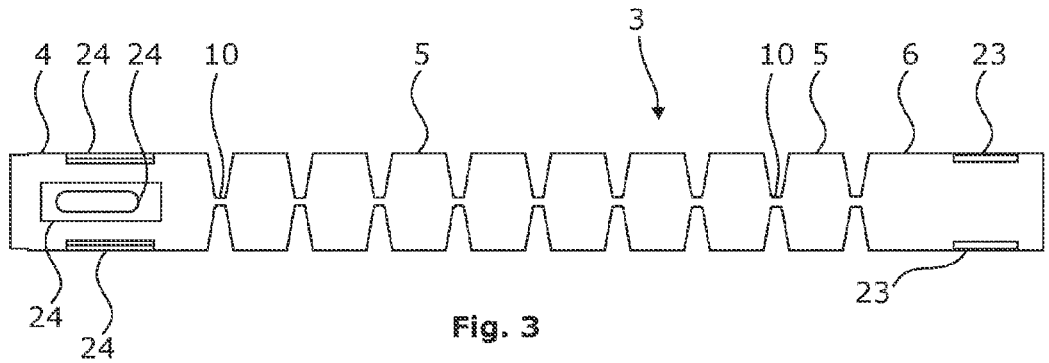
FIGS. 3 to 7 show various views of a first embodiment of the articulated tip part according to the invention.

Referring first to FIG. 1, an endoscope 1 is shown. The endoscope is disposable, and not intended to be cleaned and reused. The endoscope 1 comprises an elongated insertion tube 12. At the proximal end of the insertion tube 12 an operating handle 13 is arranged. The operating handle 13 has a control lever 14 for manoeuvring an articulated tip part 3 at the distal end of the insertion tube 12 by means of pull wires 15 (visible in FIG. 2 only). The control lever 14 is secured by means of a removable securing clip 16 to be removed before use.

Turning now to FIG. 2 details of the distal end of the insertion tube 12 with the articulated tip part 3 is shown, i.e. details from in the circle marked II in FIG. 1. Some parts, such as an external sheath normally covering the articulated tip part 3, have been removed for clarity. The articulated tip part 3 comprises a number of segments 4, 5, 6. More specifically a distal end segment 4, a proximal end segment 6 (not visible in FIG. 2) and a number of intermediate segments 5. In the illustrated embodiments, the number of intermediate segments 5 is eight, but the skilled person will understand that the precise number is less important. The distal end segment 4 comprises a camera 17, light emitting diodes 18 as well as a tube 9. The tube 9 extends inside the insertion tube 12 all the way from the distal end segment 4 of the articulated tip part 3 to the operating handle 13, so as to form a working channel. The working channel may via a suction port on the handle (not visible) be connected to a standard external suction, e.g. wall suction present in hospital environment by means of an attached tube. The external suction may be activated by means of a push-button 20 on the operating handle.

One embodiment of the articulated tip part 3 is shown in FIGS. 3 to 7 without any attached parts. It can be seen that there is one distal end segment 4 one proximal end segment 6 and eight intermediate segments 5. The segments 4, 5, 6 are interconnected by means of flexible hinge members 10, 10'. As can be seen the individual thickness of the flexible hinge members 10, 10' vary from one to the next, increasing in thickness from the distal end towards the proximal end of the articulated tip part 3, i.e. from left to right in FIG. 3. By comparison with FIG. 4, it can also be seen that flexible hinge members 10, 10' interconnecting intermediate segments are arranged in a plane corresponding to the first diameters of the cross-sections of said two adjacent segments.

Figure 4:
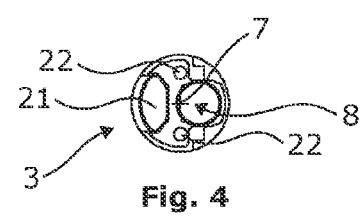

The flexibility of the articulated tip part 3 is thus higher at the distal end of the articulated tip part 3 than at the proximal end of the articulated tip part 3. The intermediate segments 5 generally have the same cross-section, which generally correspond to the end view of FIG. 4. That is to say a generally circular cross-section with four passages 8, 21, 22. The first passage 8 is circular and adapted to engage and support the outer wall of a tube 9 forming the working channel. This first passage is relatively large, and the centre 7 of the cross-section of the intermediate segments actually lies within the first passage 8. In a second embodiment of the articulated tip member 3 shown in FIGS. 8 to 12 this is even more pronounced. Cf. FIG. 9. The second passage 21 is adapted to accommodate the electrical supply wires for the camera 17 and the light emitting diodes 18, signal wires for the camera 17 etc. The camera 17 and the light emitting diodes 18 are mounted on a small circuit board to which the supply and signal wires are connected. The last two passages are pull wire passages 22 for guiding the pull wires 15. As can be seen in FIG. 4 the two pull wire passages 22 are arranged symmetrically opposite each other on either side of the plane in which the hinge members 10, 10' extend. That is to say, symmetrically opposite each other on a second diameter orthogonal to and on either side of the first diameter in each of said intermediate segments 5. At his location plenty of material surround the guide passages 22, thus giving good support for the pull wires 15 when tensioned. The ends of the pull wires are secured in the distal end section as well as connected to the control lever 14 in the operating handle 13. Thus by manipulating the control lever 14 the pull wire may be tensioned on one side of the plane of the hinge members 10, 10' and slacked on the other, thus allowing the articulated tip member 3 to bend in a desired direction.

Figure 5:
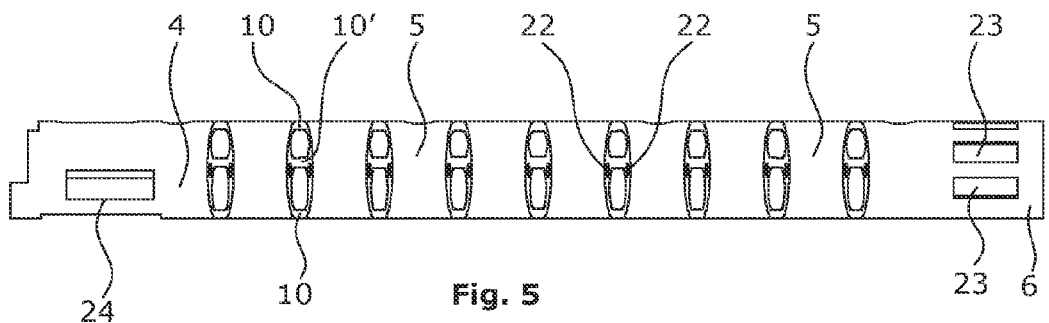
Figure 6:
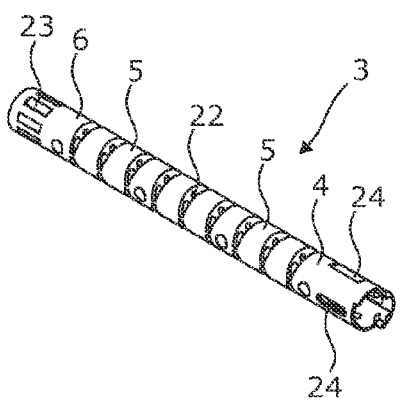
Figure 7:
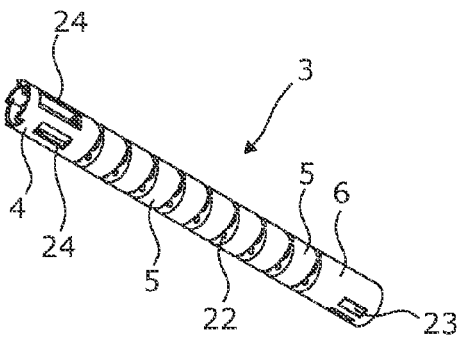

As can best be seen from FIG. 5 three hinge members 10, 10' interconnect the intermediate segments 5. The location of these hinge members 10, 10' as seen in an end view correspond to the outer walls of the intermediate segments 5 and the wall formed between the circular passage 8 and the second passage 21. There is thus two outer hinge members 10 and one central hinge member 10' interconnecting two intermediate segments 5. By having not only the outer hinge members 10 but also the central hinge member 10' allows the tube 9 forming the working channel to be supported on either side between two intermediate segments, thereby reducing the tendency of the tube 9 to kink or collapse between the intermediate segments 5, where unlike in the passages 8 it is not tightly accommodated and supported by the wall of the first passage 8.

The extra central hinge member 10' in also advantageous in another way. Were there only the lateral hinge members 10, the articulated tip member would be less resistant to torsions. More importantly there would be the risk that one or both would be compressed and two adjacent intermediate segments 5 thereby pre-bent in an undesired direction with respect to each other by external forces from e.g. the body cavity. If just one lateral hinge member 10 or even both leads to pre-bending in this uncontrolled manner, the tension from the pull wires 15 might further bend two intermediate segments 5 in the opposite direction of what is expected and desire by the operator. Having the extra central hinge member 10' mitigates this.

The proximal end segment 6 has a number of recesses or cut-outs 23 in the surface. These cut-outs aid in securing the articulated tip member 3 to the insertion tube 12 of the endoscope 1. The distal end segment 4 also has a number of cut-outs, preferably through holes 24. These help securing the camera 17, light emitting diodes 18, the end of the tube 9 etc. when these are moulded-in by means of plastic material, e.g. in a process similar to the one described in WO-A-2010/066790 incorporated herein by reference. This is particularly important when, as preferred, the articulated tip part 3 is moulded as a one-piece polypropylene member, which has good bending properties, but relatively poor adhesive properties.

As indicated above, FIGS. 8 to 12 illustrate a different embodiment of the articulated tip part 3. The difference from the first embodiment is mainly that it is adapted for a larger working channel. Consequently many parts are the same and need no repeated explanation. For the same reason corresponding reference numerals have been used. It will be noted that because the diameter of the passage 8 is larger in order to accommodate and support a larger diameter tube 9, the intermediate segments 5 as well as the distal end segment 4 and the proximal segment 6 have been made shorter as compared to the overall diameter of the cross-section of the intermediate segments 5. More specifically the outer diameter of the cross-section of the intermediate segments 5 of the first embodiment is about 4 mm and the inner diameter of the tube 9 forming the working channel about 1.2 mm, whereas in the second embodiment the outer diameter of the cross-section of the intermediate segments 5 is about 5 mm and the inner diameter of the tube 9 forming the working channel is about 2.5 mm. Furthermore the cut-outs and through holes 24 of the distal end segment 4 differ in order to better accommodate both the camera and the working channel in the distal end surface of the endoscope.

Both of the embodiments, however, have in common the feature of intermediate segments with first passages 8, adapted to accommodate and in particular support the outer wall of the tube 9 forming the working passage. That is to say, the outer diameter of the tube 9 corresponds essentially to the inner diameter of the passage 8 in the intermediate segments 5. This in turn allows the use of a working canal made from a tube, which does not have the same flexibility all the way from the operating handle 13 to the distal end of the endoscope 3. Rather, the tube 9 providing the working channel may comprise a first proximal section and a second distal section along the length thereof, wherein the second section has a higher degree of flexibility than the first section. Preferably, the material for both the first proximal section and the second distal section is polyurethane but with different flexibility.

The skilled person will understand that many variations and deviations from the above exemplary embodiments are possible without parting from the gist of the invention. In particular other materials, other dimensions, or other numbers of segments than those mentioned above could be used.

The invention claimed is:

1. An endoscope comprising: an operating handle; an insertion tube connected to the operating handle; an articulated tip part connected to the insertion tube, the articulated tip part including: a distal end segment including a camera; a proximal end segment; intermediate segments arranged between the distal end segment and the proximal end segment, each intermediate segment comprising a first passage, a second passage, and two third passages, the intermediate segments having a generally circular cross-section with a center and a radius; and flexible hinge members connecting the distal end segment, the proximal end segment, and adjacent intermediate segments of the intermediate segments, the flexible hinge members integrally molded with the adjacent intermediate segments in a one-piece part; a tube providing a working channel of the endoscope, each of the first passages of the intermediate segments having an inner diameter corresponding to an outer diameter of the tube, the first passages engaging and supporting the tube, the first passage is off-set with respect to said center, the center lies within said first passage, the inner diameter is equal to or greater than the radius and less than two times the radius; electrical wires extending from the camera to the operating handle through the second passages of the intermediate segments; and pull wires passing through the two third passages of the intermediate segments, the pull wires configured to articulate the articulated tip.

2. The endoscope according to claim 1, wherein the tube providing the working channel comprises a first section and a second section along the length thereof, wherein the second section has a higher degree of flexibility than the first section and is supported by the intermediate segments.

3. The endoscope according to claim 2, wherein at least one flexible hinge member engages and supports the second section of the tube.

4. The endoscope according to claim 2, the articulated tip part further including a central flexible hinge member connecting two of the intermediate segments, wherein at least one of the flexible hinge members and the central flexible hinge member engage and support the second section of the tube.

5. The endoscope according to claim 2, wherein a first flexible hinge member is located nearer the proximal end segment than a second flexible hinge member, and wherein the first flexible hinge member has a thickness that is greater than a thickness of the second flexible hinge member.

6. The endoscope according to claim 1, wherein each of the intermediate members comprises a circumferential wall including two thick sections and two thin sections, the two thick sections being diametrically opposite and comprising the two third passages, and the two thin sections traversed by the bending plane traversing the flexible hinge.

7. The endoscope according to claim 1, wherein the two third passages are arranged on either side of a bending plane that traverses the flexible hinge members and are configured to support pull wires configured to articulate the articulated tip part.

8. The endoscope according to claim 7, wherein some of the flexible hinge members are configured to engage and support the tube providing said working channel of the endoscope.

9. The endoscope according to claim 7, wherein the flexible hinge members have individual thicknesses that decrease from one flexible hinge member to the next flexible hinge member in a direction from the proximal end segment to the distal end segment.

10. The endoscope according to claim 7, wherein surfaces of at least some of the distal end segment, the proximal end segment, or the intermediate segments comprise recesses or cut outs.

11. The endoscope according to claim 7, wherein the flexible hinge members comprise two external hinge members disposed on a circumferential wall of the articulated tip part and a central hinge member disposed within the articulated tip part, the two external hinge members and the central hinge member connecting two of the intermediate segments, and the central hinge member configured to, together with the first passages, engage and support the tube providing the working channel of the endoscope, thereby permitting the tube to have a thinner wall and a larger diameter than possible without such engagement and support without kinking of the tube in use.

12. An endoscope comprising: an operating handle; an insertion tube connected to the operating handle; an articulated tip part connected to the insertion tube, the articulated tip part including: a distal end segment; a proximal end segment; intermediate segments arranged between the distal end segment and the proximal end segment, the intermediate segments having a generally circular cross-section with a center and a radius, wherein each of the intermediate segment comprises a circumferential wall including two diametrically opposite thick sections and two thin sections intermediate the two thick sections, the two thin sections traversed by a bending plane; and flexible hinge members integrally molded with and connecting the distal end segment, the proximal end segment, and adjacent intermediate segments of the intermediate segments in a one-piece part, the flexible hinge members comprising external hinge members extending between the two thin sections of the adjacent intermediate segments and central hinge members disposed within the articulated tip part; and a tube providing a working channel of the endoscope, each of a first passage, the central hinge members, and external hinge members are coextensive with the first passage, engaging and supporting the tube, the first passage is off-set with respect to said center, the center lies within said first passage, the inner diameter is equal to or greater than the radius and less than two times the radius.

13. The endoscope as in claim 12, wherein a first flexible hinge member is located nearer the proximal end segment than a second flexible hinge member, and wherein the first flexible hinge member has a thickness that is greater than a thickness of the second flexible hinge member.

14. The endoscope according to claim 12, wherein the tube providing the working channel comprises a first section and a second section along the length thereof, wherein the second section has a higher degree of flexibility than the first section and is supported by the intermediate segments.

15. The endoscope as in claim 12, wherein the articulated tip part has a longitudinal axis traversing the first passages.

16. The endoscope according to claim 7, wherein each intermediate segment includes a dividing wall separating the first passage and the second passage.

17. The endoscope according to claim 7, wherein each of the intermediate segments comprises an external surface and each of the flexible hinge members comprises an external surface, and wherein the external surfaces of two adjacent intermediate segments are coplanar with the external surface of the flexible hinge member positioned between the two adjacent intermediate segments.

18. The endoscope according to claim 1, wherein an external surface of the intermediate segments is coplanar with an external surface of the flexible hinge members.

19. The endoscope according to claim 12, wherein an external surface of the intermediate segments is coplanar with an external surface of the flexible hinge members.

* * * * *